United States Patent
Bacher et al.

(10) Patent No.: US 8,398,620 B2
(45) Date of Patent: Mar. 19, 2013

(54) MEDICAL INSTRUMENT WITH A ROTATABLE DETENT

(75) Inventors: Uwe Bacher, Tuttlingen (DE); Sabine Summerer, Ebersberg (DE)

(73) Assignee: Karl Storz GmbH & Co. KG (DE)

(*) Notice: Subject to any disclaimer, the term of this patent is extended or adjusted under 35 U.S.C. 154(b) by 354 days.

(21) Appl. No.: 12/762,090

(22) Filed: Apr. 16, 2010

(65) Prior Publication Data

US 2010/0268268 A1    Oct. 21, 2010

(30) Foreign Application Priority Data

Apr. 17, 2009   (DE) .................. 10 2009 018 638

(51) Int. Cl.
*A61B 17/00*    (2006.01)
(52) U.S. Cl. ........................................................... 606/1
(58) Field of Classification Search .................. 606/205, 606/206, 207, 208, 39, 45, 142, 143, 174; 623/1.11, 1.23
See application file for complete search history.

(56) References Cited

U.S. PATENT DOCUMENTS

| | | | | |
|---|---|---|---|---|
| 5,176,702 A * | 1/1993 | Bales et al. | | 606/208 |
| 5,314,424 A * | 5/1994 | Nicholas | | 606/41 |
| 5,618,294 A | 4/1997 | Aust et al. | | |
| 5,626,608 A * | 5/1997 | Cuny et al. | | 606/205 |
| 6,077,287 A | 6/2000 | Taylor et al. | | |
| 6,595,984 B1 * | 7/2003 | DeGuillebon | | 606/1 |
| 7,931,660 B2 * | 4/2011 | Aranyi et al. | | 606/143 |
| 8,137,263 B2 * | 3/2012 | Marescaux et al. | | 600/101 |
| 2002/0169446 A1 * | 11/2002 | Mulier et al. | | 606/50 |
| 2005/0159732 A1 * | 7/2005 | Rosheim | | 606/1 |
| 2007/0233053 A1 * | 10/2007 | Shelton et al. | | 606/1 |
| 2007/0299469 A1 | 12/2007 | Carpenter et al. | | |
| 2008/0154299 A1 * | 6/2008 | Livneh | | 606/205 |
| 2008/0275444 A1 * | 11/2008 | Onishi | | 606/45 |
| 2009/0131974 A1 * | 5/2009 | Pedersen et al. | | 606/205 |

FOREIGN PATENT DOCUMENTS

| | | |
|---|---|---|
| DE | 9100597 U1 | 10/1991 |
| DE | 10125149 A1 | 12/2002 |
| DE | 10232086 A1 | 1/2004 |
| WO | 2006071120 A1 | 7/2006 |

OTHER PUBLICATIONS

European Search Report; Application No. EP 10 16 0031; Aug. 13, 2010; 5 pages.

* cited by examiner

*Primary Examiner* — Ryan Severson
*Assistant Examiner* — Jonathan W Miles
(74) *Attorney, Agent, or Firm* — St. Onge Steward Johnston & Reens LLC

(57) ABSTRACT

A medical instrument comprises a shaft, a handle connected to said shaft and having a movable gripping part. An insert is guided along said shaft and connected to said movable part at its proximal end. A tool is provided at a distal end of said insert. A lock is provided for locking said movable grip part in a position. A detent is provided for releasing said locking of said lock. A rotatable stopping member is arranged on said movable grip part. A rotational plane of said rotatable stopping member lying across a longitudinal axis of a movement direction of said movable grip part. Said rotatable stopping member can be rotated between a first position not influencing said locking function of said lock and a second position keeping said lock permanently away from said locking engagement.

18 Claims, 3 Drawing Sheets

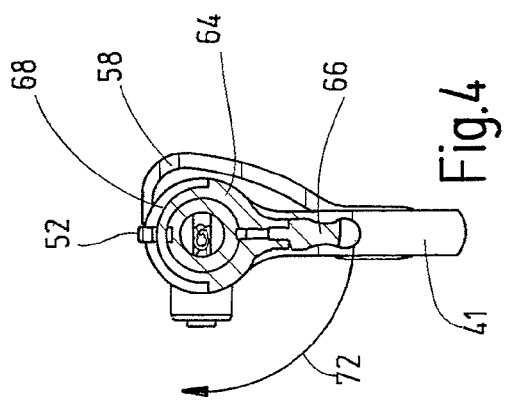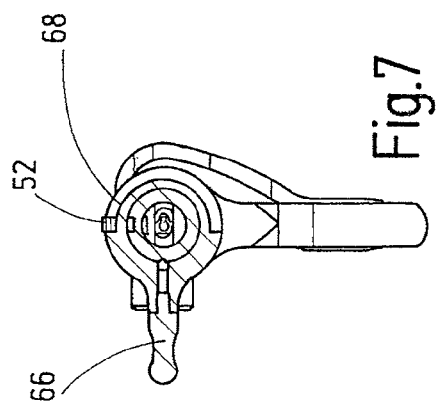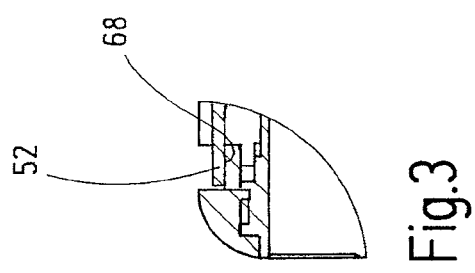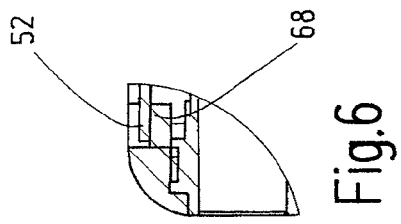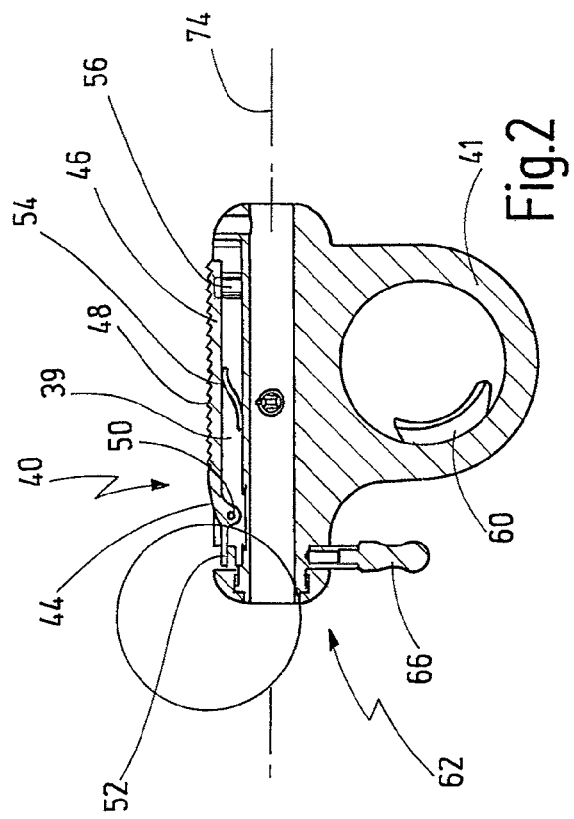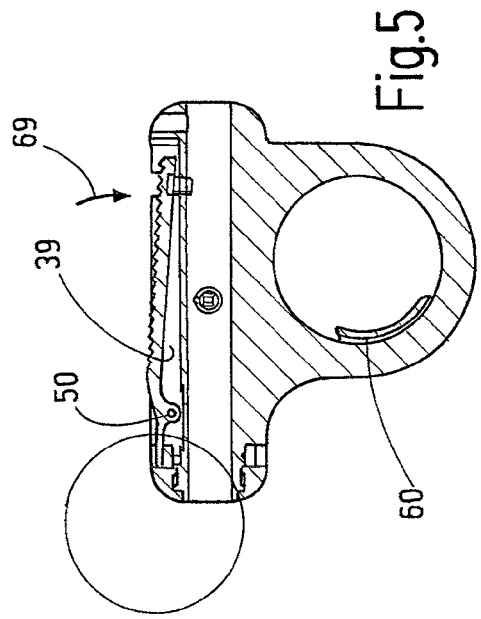

MEDICAL INSTRUMENT WITH A ROTATABLE DETENT

The present application claims priority of German patent application No. 10 2009 018 638.7 filed on Apr. 17, 2009.

BACKGROUND OF THE INVENTION

The invention relates to a medical instrument with a shaft connected proximally to a handle, with an insert guided along the shaft, which insert is connected to a moveable grip part of the handle on the proximal side and distally has a tool which can be actuated by moving the moveable grip part, and with a lock which can lock the moveable grip part in a position.

The lock can fix the moveable grip part that actuates the instrument. The lock usually consists of a rod-shaped component attached to an unmoveable grip part. On the side facing the moveable grip part, the lock has teeth which interact with a latching element on the moveable grip part.

For example, DE 102 32 086 A1 and WO 2006/071120 A1 disclose further instruments with such locks.

Such medical instruments are used particularly in minimally invasive surgery and are continuously developed in respect of use and adjustment options.

By way of example, one development consists of designing the rigid shaft such that it can bend at least in its distal end region.

Such apparatuses are known from e.g. U.S. Pat. Nos. 5,618, 294 and 6,077,287. The bendability is achieved by virtue of the fact that the distal end region has a flexible design, for example in the form of elements interconnected in a spine-like fashion. Control, i.e. bending and realigning to a straight line, is brought about by cables arranged diametrically in the shaft.

For this, a number of adjustment members are present in the region of the handle or the grip parts. That is to say, there are adjustment members for deflecting the shaft, adjustment members for moving the grip part, adjustment members for opening and closing the locking function and the like. There is ambition to arrange these adjustment members in the region of the handle where possible such that an operator, who has picked up the instrument by the handle, can operate the various adjustment members using his/her fingers.

However, care has to taken in this case that these adjustment members are arranged as ergonomically as possible and are also unambiguous so that a wrong adjustment member is not inadvertently operated during a surgical intervention.

In the case of combined dissecting/gripping forceps, it is desirable for the jaw parts of the tool to be able to be moved freely for the duration of the dissecting process, i.e. the latter should not be interrupted by an inadvertently triggered other function.

After the dissection, e.g. severing a piece of tissue, it then is desirable for this severed piece of tissue to be held between the jaw parts, with a certain amount of contact pressure and holding pressure having to be exerted and the tissue being intended to be held in this state. This hold should ensure that the held piece of tissue is not lost during further manipulations, but that it can be pulled away from the body during a minimally invasive intervention, for example through a trocar cannula sticking in the body. If, for example, the dissecting process and the subsequent gripping process were carried out in an angled state of the shaft, the latter would firstly have to be aligned in a straight line so that it can be pulled out through a trocar cannula.

Thus, an object of the present invention is to develop a medical instrument, particularly an instrument with a shaft that can be angled, to the end of affording functionally reliable and ergonomic handling, particularly in respect of the locking and the release of the locking of the moveable grip part.

SUMMARY OF THE INVENTION

According to the invention, the object is achieved by a medical instrument comprising a shaft, a handle connected to said shaft and having a movable grip part, an insert guided along said shaft, said insert being connected to said movable grip part at its proximal end, a tool provided at a distal end of said insert, said tool can be actuated by moving said movable grip part, a lock for locking said movable grip part in a position, a detent for releasing said locking of said lock, said detent permanently releases a locking function of said lock, a rotatable stopping member arranged on said movable grip part, a rotational plane of said rotatable stopping member lying across a longitudinal axis of said movement direction of said movable grip part, wherein said rotatable stopping member can be rotated between a first position not influencing said locking function of said lock and a second position keeping said lock permanently away from a locking engagement.

These measures have a number of advantages in respect of functional reliability and ergonomics. The advantage of arranging the rotatable stopping member on the moveable grip part is that in all pivoting, displacement or other positions of the moveable grip part, the stopping member is always in a certain relative position thereto. The handling person can move the moveable grip part, which for example opens and closes the jaw parts, to-and-fro in a conventional manner, be it by pivoting or a linear to-and-fro movement, without the rotatable stopping member being required in the process. Should the locking function be lifted permanently, it is possible to detect the rotatable stopping member on the moveable grip part by a finger and said member can be rotated accordingly. As a result of the rotational plane running across the longitudinal axis of the movement direction of the grip part, the rotatable stopping member cannot be moved inadvertently whilst moving the grip part because a finger of the hand has to carry out a completely different movement for this. Grip parts conventionally have a finger ring, into which the finger is inserted to move said grip part. The handling person must now either very definitely use a different finger to move the rotatable stopping member, or firstly remove the finger already sticking in the finger ring therefrom and use it to move the rotatable stopping member. This primarily satisfies the safety of operation.

The rotational movement as such is a movement that can be carried out without jerks and ergonomically. It is easy and thus ergonomic to provide two different positions in which two different functions are possible, namely firstly not to influence the locking function of the lock and, in the second position, to keep the lock permanently away from the locking engagement. This can reliably be felt or gripped and touched from the handling position. If the lock is engaged, i.e. if the grip parts are latched relative to one another, it is clear that the rotatable stopping member is in the first position, because the detent has no influence on the locking function of the lock in this position. The rotatable stopping member then only has to be moved until the second position is reached, which can easily be indicated by a stop, for example. This then ensures that the lock is now permanently kept away from the locking engagement. This can be felt by virtue of the fact that the moveable grip part can be moved without the function of the lock. This can also be brought about without great attentiveness, i.e. without visual contact, because the ergonomic arrangement of the rotatable stopping member on the moveable grip part allows an appropriate rotation of the rotatable stopping member without visual contact.

Thus both requirements, i.e. relating to both operational safety and ergonomics, are satisfied.

In a refinement of the invention, the rotatable stopping member is designed as a rotary ring arranged distally in front of a finger ring of the moveable grip part.

This refinement is simple from a mechanical point of view and a rotary ring can be moved softly and without jerks. The arrangement distally in front of the finger ring allows the handling person to twist this rotary ring with either the finger located in the finger ring or the finger lying closest next to it. For example, if the index finger has been inserted into the finger ring of the moveable grip part, the middle finger can move the rotary ring arranged distally in front of said part without problems.

In a further refinement of the invention, a rod protrudes radially from the rotary ring and it can be used to rotate the rotary ring.

The advantage of this measure is that such a protruding rod can be felt very easily without visual contact and that said rod can be moved by one finger. This should be considered a particularly expedient refinement in terms of ergonomics.

In a further refinement of the invention, in the first rotational position, the rod extends in a plane of the finger ring of the moveable grip part.

The considerable advantage of this measure is that the rod extends in and is hidden virtually behind or in front of the finger-ring plane and thus does not impede manipulations such as inserting and removing the finger into and from the finger ring.

In a further refinement of the invention, in the second position, the rod extends laterally away from the moveable grip part.

From an ergonomic point of view, this can be achieved in a particularly simple and expedient fashion. For example, if the index finger is in the moveable grip part, this lateral twisting of the ring can very easily be brought about using the middle finger by the latter being placed laterally on the rod and pivoting said rod to the side.

In this laterally pivoted position, the rod can also be felt and grasped in a simple fashion in order then again to be moved securely and ergonomically to the grip part during the opposing movement.

In a further refinement of the invention, the pivoting range is approximately 90°.

This pivoting range gives the handling person good feedback about the two positions, i.e. said person only has to move the lever or the rotary ring to-and-fro between these two positions, pivoted by about 90°. This in turn can very easily be accomplished by a finger of a hand in any case holding the instrument by the handle.

In a further refinement of the invention, a mechanism is arranged in the moveable grip part and it allows the locking function of the lock to be lifted in the first rotational position of the stopping member.

The considerable advantage of this measure is that the additional mechanism allows brief lifting of the locking function if for example, the handling person wishes a slight correction in the position of the jaw parts. In this case, it is not the rotatable stopping member that has to be rotated, but the mechanism can be actuated briefly, for example for only one or two seconds and then this releases the locking function of the lock for this brief period.

If this mechanism is released again, the lock can immediately return into the locking position and reassume the locking function. Of course, this is possible because the rotatable stopping member does not influence the locking function of the lock in the first rotational position.

In a further refinement of the invention, the mechanism has a rocker lever which is operatively connected to the lock.

Now, from an ergonomic point of view, the advantage of this measure is that a rocker lever constitutes a different type of mechanism than a rotatable stopping member, and so again it is ensured in this case that feeling and movement allows easy recognition of which adjustment member is used for lifting the locking function, namely the rocker lever for brief lifting or the rotatable stopping member for permanent lifting. This contributes to the safety of the function in particular.

In a further refinement of the invention, the rocker lever has a pushbutton arranged in the finger ring of the moveable grip part.

From an ergonomic point of view, the advantage of this is that the finger sticking in the finger ring can actuate the pushbutton in order to lift the locking function briefly. If the pushbutton is released, the lock relatches immediately. If the handling person wishes to lift the locking function permanently, the detent in the form of the rotatable stopping member is moved. The latter is situated next to the finger ring of the moveable grip part and so, as a result of this, there cannot be any confusion and this increases the operational safety. This is also very ergonomic because these are two completely different components to be used by the handling person, namely a pushbutton on the one hand and a rotatable ring on the other hand, which can easily by determined by the sense of touch or haptic perception. Thus, this refinement also contributes particularly to the ergonomics.

As mentioned above, it is particularly advantageous that pushing the pushbutton lifts the lock from the locking position and releasing the pushbutton returns the lock into the locking position.

In a further refinement of the invention, the lock is designed as a two-armed lever, wherein a first lever arm supports latching teeth engaging in a locking manner with a latching element on the handle.

The considerable advantage of this measure is that the lock is formed by an element with a simple design, namely the two-armed lever, and locking or releasing the lock can be implemented by a simple pivot of the lever.

In a further refinement of the invention, the moveable grip part can be moved along a linear guide along the handle, and the latching teeth of the two-armed lever arranged on the moveable grip part face the latching element.

This refinement affords a compact and operationally reliable design.

In a further refinement of the invention, the lock is pretensioned by a spring such that the lock is pushed into the locking engagement.

The advantage of this measure is that there is a positive control of the lock into the locking position.

In a further refinement of the invention, the rotatable stopping member has a circumferential radially increasing cam face which lifts the first lever arm with the latching teeth from the latching tooth when rotated from the first rotational position into the second rotational position.

The advantage of this measure is that such a cam face brings about a jerk-free lifting movement of the first lever arm with the latching teeth away from the latching tooth.

This is a harmonic movement and not a jerked movement and thus very ergonomic.

In a further refinement of the invention, the cam face engages with the second lever arm of the two-armed lever.

The advantage of this measure is that it is not the lever arm of the two-armed lever provided with the latching teeth engaging with the cam face, but the opposite second lever arm of the two-armed lever. Thus, the entire first lever arm is available for the locking function.

In a further refinement of the invention, the rocker lever engages with the first lever arm of the two-armed lever.

In terms of design and operational safety, the significant advantage of this measure is that the mechanical connection of the rocker lever to the first lever arm supporting the latching teeth creates a direct mechanical connection for briefly lifting the lock from the locking engagement. Since this occurs in the first position of the rotatable stopping member, in which the locking function of the lock is not influenced, the second lever thus can freely be lifted from the cam face. Only once the rotatable stopping member is rotated is the lock forcefully removed permanently from the locking engagement, i.e. the rotatable stopping organ then in this sense overrides the control function of the rocker lever for the brief release of the lock.

Thus, the interaction of these two mechanisms is functionally very reliable and also can be brought about in a correspondingly ergonomic fashion because this override means that it does not have to be ensured that the rocker lever still has to be additionally moved. The latter is then automatically moved as well by the two-armed lever if the second lever arm is moved by the cam face.

It is understood that the aforementioned features and the features yet to be explained below can be used not only in the specified combinations, but also in other combinations or on their own, without departing from the scope of the present invention.

BRIEF DESCRIPTION OF THE DRAWINGS

The invention will be described in more detail and explained on the basis of a selected exemplary embodiment in conjunction with the appended drawings, in which FIG. 2 shows a section through the moveable grip part of the instrument in FIG. 1, which has the detent mechanism, to be precise in the first position of the detent, FIG. 3 shows a very-much enlarged illustration of the region circled in FIG. 2, FIG. 4 shows a front view of the grip part in FIG. 2 from distal to proximal, FIG. 5 shows an illustration comparable to FIG. 2, wherein the detent mechanism is in the second position, FIG. 6 shows a very-much enlarged illustration of the region circled in FIG. 5, FIG. 7 shows a front view of the grip part comparable to FIG. 4, with a stopping member pivoted by approximately 90°.

DETAILED DESCRIPTION OF PREFERRED EMBODIMENTS

Figure 1:
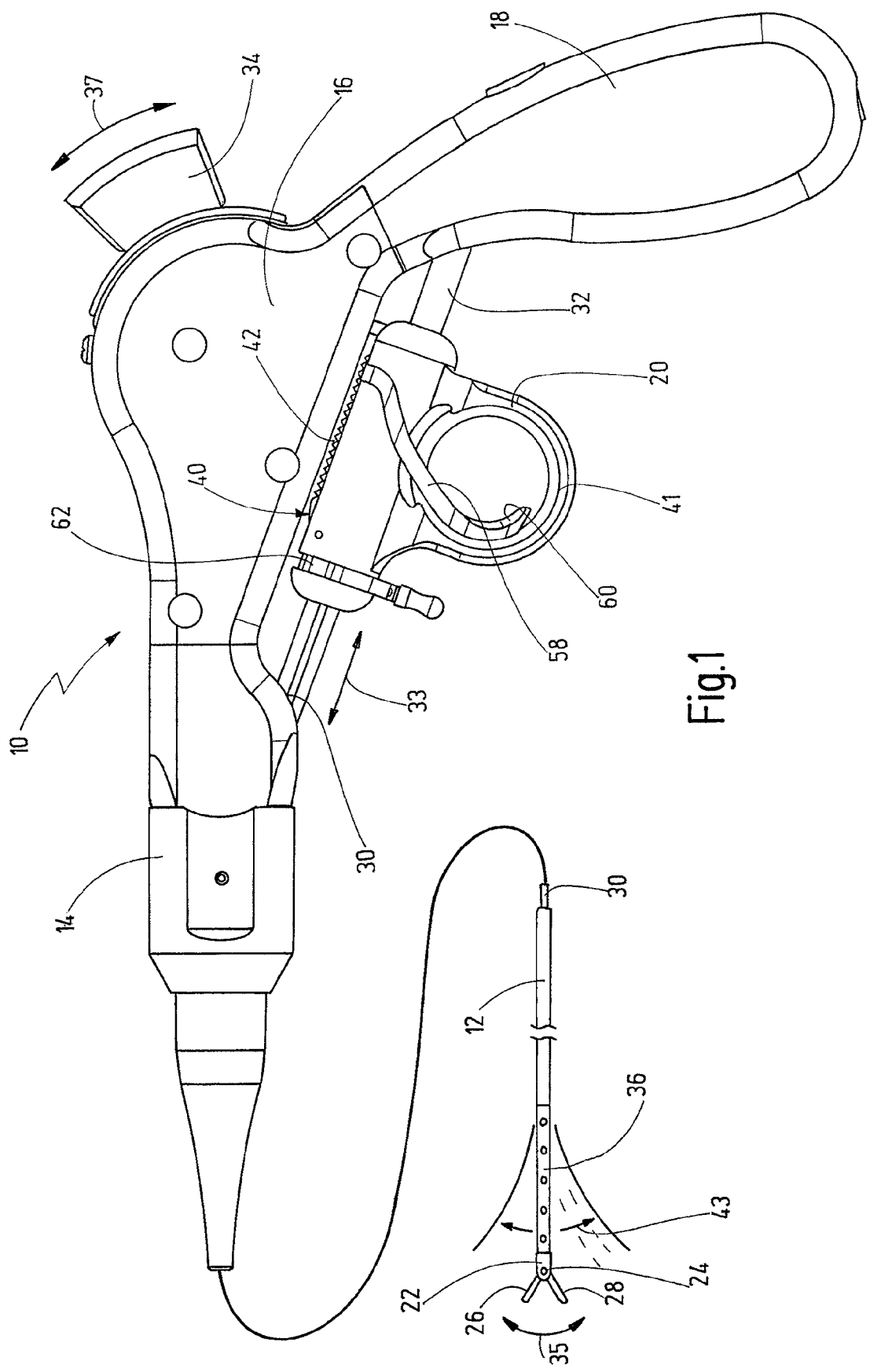
FIG. 1 shows a side view of a medical instrument provided with a detent according to the invention.

A medical instrument illustrated in FIG. 1 is referred to in its entirety by the reference symbol 10.

The instrument 10 has an elongate shaft 12 connected on the proximal side to a handle 14. The handle has a housing 16 from which a fixed grip part 18 protrudes.

A moveable grip part 20 is arranged on the housing 16, which grip part can be moved to-and-fro along a guide 32, as indicated by a double-headed arrow 33.

The shaft 12 holds a tool insert 22, which supports a tool 24 on its distal side. The tool 24 has two jaw parts 26 and 28 that can be spread and work as a combined dissecting/gripping forceps. The tool insert 22 has a rod-shaped or wire-shaped actuation member 30, which extends from the tool 24 in the interior of the shaft 12 into the housing 16 and from there it extends through the guide 32 designed as a tube to the moveable grip part 20. The proximal end of the actuation member 30 is connected to the moveable grip part 20.

Furthermore, it emerges that, protruding from the upper side of the housing 16, there is another adjustment member 34 which can be displaced to-and-fro along an orbit not referenced here, as indicated by a double-headed arrow 37. The adjustment member 34 is connected by two control cables likewise guided through the housing 16 and through the shaft 12 to a deflectable section 36 at the distal end of the shaft 12. These control cables are not indicated in any more detail here. If the adjustment member 34 is moved in one direction of the double-headed arrow 37, one of the two control cables is wound onto a drum or a drum section, and the other cable is simultaneously unwound. This deflects the deflectable section 36 in the direction of the arrow 43, for example. If the adjustment member 34 is moved in the opposite direction, the deflected section is firstly realigned to be straight and, in the case of further movement, it is then deflected in the opposite direction.

During operation, a person grips the instrument 10 with a hand on the fixed grip part 18 and places a finger, e.g. the middle finger, into a finger ring 41 of the moveable grip part. The adjustment member 34 can be moved by the thumb in order to deflect the deflectable section 36 at the distal end region of the shaft accordingly, as mentioned above. The to-and-fro movement of the moveable grip part 20 along the guide 32 linearly displaces the actuation member 30 and, in the process, opens and closes the jaw parts 26 and 28 depending on the direction, as indicated by the double-headed arrow 35.

Figure 9:
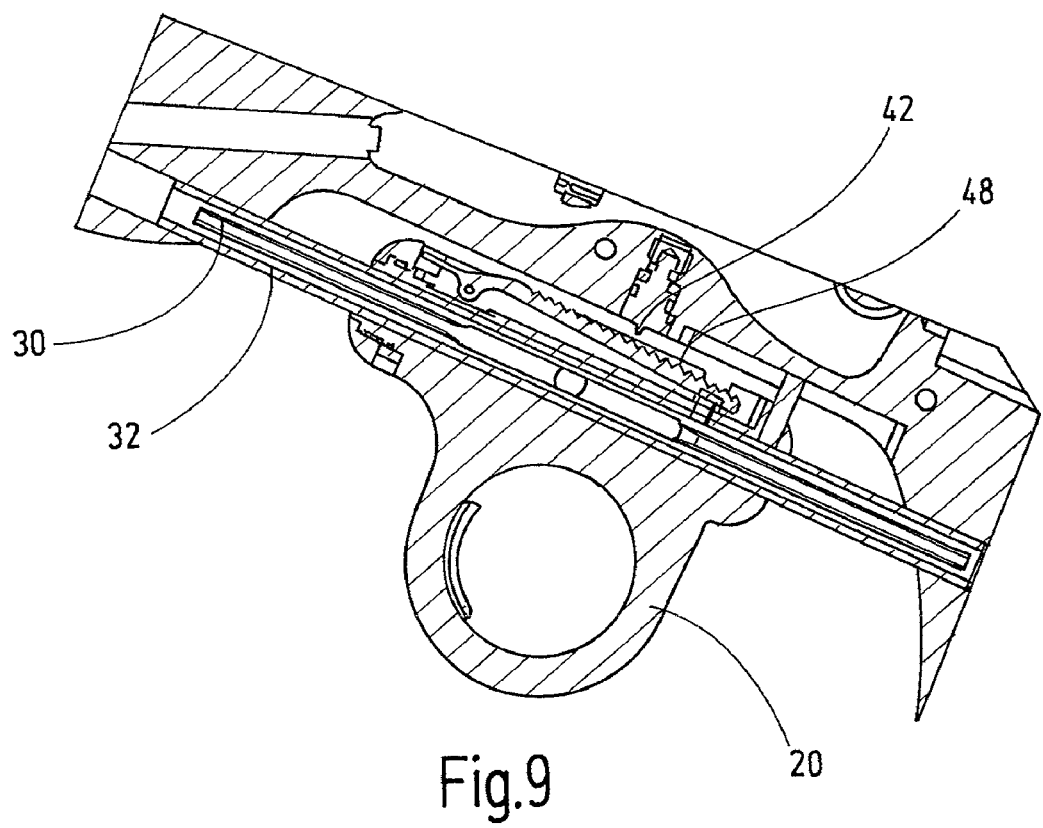
FIG. 9 shows a sectional partial section of the instrument in FIG. 1 in the region of the moveable grip part, with the detent in this case being illustrated as being in its second rotational position.

FIG. 1 and, in particular, the sectional illustration in FIG. 2 show that a lock 40 is arranged in the body of the moveable grip part 20 and it interacts with a latching element 42 protruding from the housing 16 in the direction of the moveable grip part 20 or the lock 40 thereof (see FIG. 9).

The latching element 42 is designed plainly and simply as a single fixed protruding latching tooth.

Figure 8:
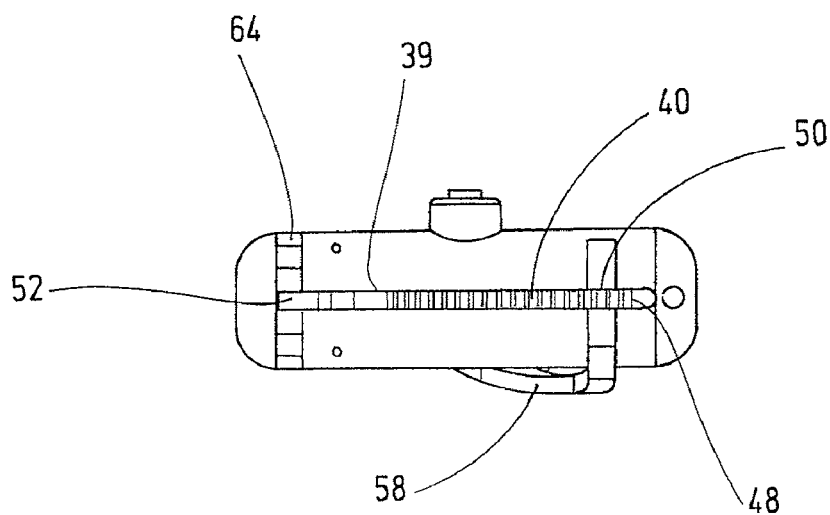
FIG. 8 shows a plan view of the moveable grip part in the first position of the detent illustrated in FIG. 2.

The sectional illustration in FIG. 2 and the plan view in FIG. 8 show that a recess 39, in which the lock 40 is held, is present on the end of the moveable grip part 20 facing the housing 16.

The lock 40 is designed as a two-armed lever 44, the first lever arm 46 of which carrying a row of latching teeth 48 on the side facing the latching element 42. The two-armed lever 44 can be pivoted about a pivot pin 50. Diametrically opposite to the first lever arm 46, an admittedly significantly shorter second lever arm 52 extends away from the pivot pin 50.

FIG. 2 and FIG. 8 in particular show that the two-armed lever extends in the direction of the longitudinal axis 74 of the guide 32, i.e. in the direction of the movement of the moveable grip part 20.

The outer end of the first lever arm 46 is fixedly connected to a rocker lever 56, which has an arm 58 extending to the side of the finger ring 41, as can be seen, in particular, in FIG. 1 and FIG. 4. The arm 58 reaches through the finger ring 41 and has a pushbutton 60 at its end side, the latter protruding into the inner space of the finger ring 41.

FIGS. 2 and 4 show that the stopping member 62 according to the invention is arranged distally in front of the finger ring 41.

The stopping member 62 has a ring 64, from which a rod 66 extends away in the radial direction.

The ring 64 is inserted in a ring groove (not referred to in any more detail here) on the moveable grip part and the inner cavity of the guide 32 is enclosed thereby.

An outer side of the ring 64 is designed as a cam face 68. The enlarged section in FIG. 3 in particular shows that the lower side of the second lever arm 52 is borne by the cam face 68. This bearing is defined, inter alia because there is a spring 54 between the lower side of the first lever arm 46 and the base of the recess 39 and said spring is pretensioned such that it pushes the first lever arm 46 in the direction of the housing 16 or the latching element 42 thereof. That is to say, the spring 54 pretensions the lock 40 in the direction of the locking position. The lever 44 itself can be designed as a compression spring, or a spring can be placed around the pivot pin 50 of said lever.

In the position illustrated in FIGS. 1 and 2, the stopping member 62 is in its first position in which the locking function of the lock 40 remains uninfluenced.

That is to say, as mentioned above, the lock is pushed by the spring 54 in the direction of locking engagement with the latching element 52, as is illustrated, for example, in FIG. 1.

Pushing the pushbutton 60 can move the rocker lever 56, which pulls the first lever arm 46 of the lock 40 slightly into the recess 39 during the rocking movement, and so this first lever arm is moved out of the locking engagement with the latching element 42.

During this movement, the second lever arm 52 can lift off the cam face without problems, as shown in FIG. 3 for example. When the pushbutton 60 is released again, the first lever arm 46 is once again pushed into the locking engagement with the latching element 42 by the spring 54.

Thus, the rocker lever 56 serves only for brief lifting of the locking function.

If this locking function should be lifted permanently, the stopping member 62 is pivoted by approximately 90° to the side, as can be seen from the transition from FIG. 4 to FIG. 7 and is indicated by an arrow 72 in FIG. 1.

The cam face 68 is designed such that it increases in the radial direction.

FIG. 6 in particular shows that if the ring 64 was moved into the position illustrated in FIG. 7, the second lever arm 52 is lifted so far that the opposite first lever arm 46 is moved into the recess 39, i.e. out of the locking engagement with the latching element 42.

This situation is illustrated in FIG. 5.

FIG. 5 also shows that the first lever arm 46 moved into the recess 39 has moved the rocker lever 56 such that the pushbutton 60 has likewise moved.

That is to say, the stopping member 62 overrides this mechanism, which can be triggered by the rocker lever 56 or the pushbutton 60.

This rotational movement can be carried out very ergonomically, as is easily understandable from the transition from FIG. 4 to FIG. 7.

FIG. 7 in particular shows that, in the second position, the rod 60 protrudes laterally from the moveable grip part 20 but nevertheless nestles against the lower side of the housing 16. Stated differently, the rod 60 does not block any further handling of the instrument 10 in this position.

The position illustrated in FIGS. 5, 6 and 7 corresponds to the second position, i.e. in which the locking function has been lifted permanently.

Thus, the stopping member 62 acts as a permanent detent. The plane prescribed by the arrow 72 in FIG. 4 thus corresponds to the rotational plane 72 of the ring, which is situated transversely in front of the finger ring 41 of the moveable grip part 20.

If, as described above, a handling person holds the instrument 10 with one hand, e.g. the right hand, and has inserted the middle finger into the finger ring 41, the ring 46 can be rotated by 90° without problems using the index finger by gripping the rod 66 with the finger, i.e. the transition from FIG. 4 to FIG. 7 can be accomplished. In the process, the instrument does not have to be released, and e.g. the thumb is still available for actuating the adjustment member 34, for example.

In this second position of the detent, the moveable grip part 20 can now freely be moved to-and-fro along the guide 32, as is shown in particular in the sectional view in FIG. 9.

The component illustrated in FIG. 2 or 5, i.e. the moveable grip part 20, is also often referred to as a trigger in the art.

In this second position, in which the locking function has permanently been lifted, the operator, for example, can perform a dissecting procedure by, for example, correspondingly dissecting, i.e. severing, a tissue or a cyst or a tumour using the jaw parts 26 and 28. Once this piece of tissue has been severed, it should be held between the jaw parts 26 and 28, for which purpose this piece of tissue should be brought into a very particular position, which should then remain unchanged in order to ensure that the severed piece of tissue is held between the two jaw parts 26 and 28. For this, the detent then is moved again from the second position into the first position, i.e. it undergoes the transition from FIG. 7 to FIG. 4.

Now, the first lever arm 46 can again latch into the latching element with its locking hands 48, and a to-and-fro movement of the trigger along the guide 32 is locked.

Different manipulations can now be carried out. For example, if the shaft 12 was deflected laterally, it firstly can be brought into a linearly aligned position using the adjustment member 34 again in order subsequently to withdraw the shaft again, which shaft is inserted into a body cavity through a trocar during a minimally invasive intervention. In the process, the lock permanently remains in its latched position and thus ensures that the jaw parts 26 and 28 hold the tissue kept therebetween during these manipulations and do not lose said tissue. Should the handling person desire e.g. a slight increase in the contact pressure between the jaw parts 26 and 28, the trigger can be moved along by one tooth in order to move the moveable grip part 20 by one tooth width.

It is understood that said user could also carry out the reverse movement procedure if the user for example determines that the jaw parts 26 and 28 are gripping the tissue too strongly and there is a risk of the tissue being divided into two parts. Then, brief pushing of the pushbutton 60 allows a reaction in, so to speak, the other direction and a displacement of one tooth width in the opposite direction for a slight reduction in the contact pressure.

The invention claimed is:

1. A medical instrument, comprising
a shaft,
a handle connected to said shaft, said handle having a movable grip part and a fixed grip part, said movable grip part able to move in a path;
a tool insert guided along said shaft, said insert being connected to said movable grip part at its proximal end, a tool provided at a distal end of said insert, said tool able to be actuated by moving said movable grip part, a lock for locking said movable grip part in a position, a detent for releasing said locking of said lock, said detent able to permanently release a locking function of said lock, a rotatable stopping member arranged on said movable grip part, said rotatable stopping member able to move in a rotational plane, the rotational plane extending perpendicular or substantially perpendicular to said path of said movable grip part, said rotatable stopping member able to be rotated between a first position not influencing said locking function of said lock, and a second position keeping said lock permanently away from a locking engagement.

2. The medical instrument of claim 1, wherein said rotatable stopping member is designed as a rotary ring arranged distally in front of a finger ring of said movable grip part.

3. The medical instrument of claim 2, wherein a rod protrudes radially from said rotary ring and said rod can be used to rotate said rotary ring.

4. The medical instrument of claim 3, wherein in said first rotational position of said rotatable stopping member said rod extends in a plane of said finger ring of said movable grip part.

5. The medical instrument of claim 4, wherein in said second position said rod extends laterally away from said movable grip part.

6. The medical instrument of claim 1, wherein a range through which said rotatable stopping member can be rotated is approximately 90°.

7. The medical instrument of claim 1, wherein a mechanism is arranged in said movable grip part, said mechanism allowing a locking function of said lock to be lifted in said first rotational position of said stopping member.

8. The medical instrument of claim 7, wherein said mechanism has a rocker lever which is operatively connected to said lock.

9. The medical instrument of claim 8, wherein said rocker lever has a pushbutton arranged in a finger ring of said movable grip part.

10. The medical instrument of claim 9, wherein a pushing of said pushbutton lifts said lock from said locking position and releasing said pushbutton returns said lock into said locking position.

11. The medical instrument of claim 1, wherein said lock is designed as a two-armed lever, with a first lever arm supporting latching teeth engaging in a locking manner with a latching element on said handle.

12. The medical instrument of claim 11, wherein said movable grip part can be moved along a linear guide along said handle, and wherein said latching teeth of said two-armed lever face said latching element.

13. The medical instrument of claim 1, wherein said lock is pretensioned by a spring such that said lock is pushed into said locking engagement.

14. The medical instrument of claim 13, wherein said rotatable stopping member has a circumferential radially increasing cam face which lifts a first lever arm with latching teeth from a latching element when rotated from its first rotational position into its second rotational position.

15. The medical instrument of claim 14, wherein said cam face can engage with a second lever arm of a two-armed lever.

16. The medical instrument of claim 15, wherein a rocker lever engages with said first lever arm of said two-armed lever.

17. The medical instrument of claim 1, wherein said movable grip part is able to move along a longitudinal axis between said fixed grip part and said shaft.

18. The medical instrument of claim 1, wherein said movable grip part is able to move by pivoting.

\* \* \* \* \*